United States Patent [19]

Luoma, II

[11] Patent Number: 5,389,265
[45] Date of Patent: Feb. 14, 1995

[54] PHASE-SEPARATION TUBE

[75] Inventor: Robert P. Luoma, II, Newark, Del.

[73] Assignee: E. I. Du Pont de Nemours and Company, Wilmington, Del.

[21] Appl. No.: 71,137

[22] Filed: Jun. 2, 1993

[51] Int. Cl.⁶ .................. B01D 17/038; B01D 17/12
[52] U.S. Cl. .................... 210/745; 210/94;
  210/789; 422/72; 422/82.05; 436/45
[58] Field of Search ............... 210/94, 512.1, 516,
  210/745, 787, 789; 422/72, 82.05, 58, 102;
  436/45, 164

[56] References Cited

U.S. PATENT DOCUMENTS

| 3,814,522 | 6/1974 | Clark et al. | 422/102 |
|---|---|---|---|
| 3,887,464 | 6/1975 | Ayers | 210/117 |
| 4,066,414 | 1/1978 | Selby | 422/102 |
| 4,105,415 | 8/1978 | Lovett | 422/58 |
| 4,917,801 | 4/1990 | Luderer et al. | 210/516 |
| 5,053,134 | 10/1991 | Luderer et al. | 210/516 |
| 5,260,032 | 11/1993 | Muller | 422/72 |
| 5,271,852 | 12/1993 | Luoma | 210/789 |
| 5,275,731 | 1/1994 | Jahn | 210/516 |
| 5,282,981 | 2/1994 | Adams et al. | 210/789 |
| 5,308,506 | 5/1994 | McEwen et al. | 210/789 |

Primary Examiner—Joseph W. Drodge

[57] ABSTRACT

A tube and method of partitioning a pre-selected phase of a sample of liquid having a plurality of phases of differing densities. The tube has a smaller diameter at one end. In use, a sample of liquid is passed through a first end of a linear tube and into a first chamber of said tube. The first chamber is located at the first end of the tube and is separated from a second chamber located at a second opposed end of the tube by a separation device. The separation device slidably engages the interior surface of the tube in an essentially fluid-tight manner and has a flow-restriction orifice therein to permit fluid flow communication between the first and second chambers under the influence of force. The phases are then ordered within the tube using e.g. axial centrifugation. The volume of the first chamber is reduced by movement of the separation device within the tube, such that one phase of the liquid in the first chamber flows through the flow-restriction orifice and into the second chamber. The method is monitored using the section of the tube that has the smaller diameter.

17 Claims, 3 Drawing Sheets

PHASE-SEPARATION TUBE

FIELD OF THE INVENTION

The present invention relates to a phase-separation tube and its use in the separation into phases of a sample of liquid, including colloidal suspensions, having a plurality of phases of differing densities and optical characteristics, and especially for the separation of one phase of the liquid sample from the remainder of the liquid in a manner that minimizes contamination of the phases and contamination of a phase of the liquid with the liquid per se. The invention is especially useful in the separation of blood into components thereof, for example for purposes of testing and analysis of blood components, while minimizing contamination of a separated phase by the whole blood. The tube is a double-ended tube that is particularly adapted for sensing the separation of phases.

BACKGROUND OF THE INVENTION

Diagnostic tests frequently require separation of a patient's whole blood sample into components, especially cellular portions from non-cellular portions e.g. serum or plasma from cells. For instance, plasma is obtained from anticoagulated blood and still contains all of the coagulation proteins, whereas serum is obtained from clotted blood with the proteins being retained with the clot and red blood cells. Samples of whole blood are typically collected by venipuncture through a special cannula or needle attached to a syringe or an evacuated collection tube. The sample of blood that is to be separated into components is typically drawn, using a needle, through a penetrable self-sealing elastomeric closure or other stopper into an evacuated tube. Separation is then accomplished e.g. by rotation of the tube in a centrifuge.

The centrifuge may be a conventional centrifuge e.g. a swinging bucket or a fixed angle centrifuge, as the different components of the whole blood have different densities, as described in U.S. Pat. No. 4,152,269 of A. L. Babson. Alternatively, the centrifuge may be an axial centrifuge i.e. a centrifuge in which separation of the phases is achieved by rotation of the tube about its longitudinal axis i.e. axial rotation, as described in U.S. Pat. No. 4,828,716 of J. A. McEwen et al. In the latter process, the blood sample is introduced to the tube through a cap assembly that consists of a piercable closure and a separator that has a one-way valve. The tube is then rotated about its longitudinal axis; the heavier cellular phase lines the tube wall and thereby separates from the lighter non-cellular (plasma or serum) phase. Once separation has been achieved, an axial probe penetrates the piercable closure, detaches the separator from the closure and forces the separator down the tube. The axially-located non-cellular phase passes through the separator. An optical sensor is utilized to detect when the cellular phase begins passing into the separator, and to stop movement of the separator. Thus, the two phases are physically separated.

A known separator that is believed to be effective in maintaining the phases in a physically separated form is disclosed in copending U.S. patent application of G. A. Adams and R. P. Luoma, No. 07/877,496, filed May 01, 1992, now U.S. Pat. No. 5,282,198, A double ended tube for use in an axial centrifuge is disclosed in copending U.S. patent application of R. P. Luoma, No. 07/887,497, filed May 01,1992 now U.S. Pat. No. 5,271,852.

In routine operation of an axial separation process, it is important that the process be capable of being controlled in a consistent manner, in addition to the need to minimize and preferably avoid cross-contamination of samples.

SUMMARY OF THE INVENTION

Accordingly, the present invention provides a tube for the partitioning and separation of a pre-selected phase of a sample of liquid having a plurality of phases of differing densities and optical characteristics, said tube being linear and having sealable openings at first and second opposed ends thereof, the first end of the tube being of smaller diameter than the second end, said smaller diameter extending away from the sealable opening at the first end for a minor fraction of the length of the tube and being optically transparent, a separation device located within the tube that separates the tube into at least two chambers at opposed ends of the tube, said separation device being located at the second end of the tube and slidably engaging the interior surface of the tube in an essentially fluid-tight manner, the separation device having an orifice therethrough for fluid flow communication between the chambers, said orifice having a flow-restriction channel.

In a preferred embodiment of the tube of the invention, a minor fraction of the length of the tube has walls that in part are parallel to the longitudinal axis of the tube.

In another embodiment, the tube at locations other than the first end is of constant diameter and cross-section.

In further embodiments of the invention, the second chamber is an incipient chamber that forms as the separation device is moved along the tube and away from the first end.

The present invention also provides a method of partitioning a pre-selected phase of a sample of liquid having a plurality of phases of differing densities and optical characteristics, comprising the steps of:

(a) passing said sample of liquid through a first end of a linear tube and into a first chamber of said tube, said first chamber being located at the first end of said tube and being separated from a second chamber located at a second opposed end of said tube by a separation device, said second chamber being free of the liquid, said separation device slidably engaging the interior surface of the tube in an essentially fluid-tight manner and having a flow-restriction orifice therein to permit fluid flow communication between the first and second chambers under the influence of force, said first end of the tube being of smaller diameter than the second end, said smaller diameter extending away from the sealable opening at the first end for a minor fraction of the length of the tube;

(b) ordering the phases of the sample within the tube using axial centrifugation;

(c) while the phases are ordered, reducing the volume of the first chamber by movement of the separation device within the tube, such that one phase of the liquid in the first chamber flows through the flow-restriction orifice as the volume of the first chamber is reduced and into the second chamber, said phase in the second chamber being removable therefrom through the second end of the tube; and (d) monitoring at least one phase by optical means fixedly located proximate the section of the tube of smaller diameter and controlling the reduction in volume according to the results of the monitoring of said phase.

In a preferred embodiment of the method of the invention, the flow-restriction channel permits flow of liquid from the first chamber to the second chamber during step (c) but restricts flow of liquid at other times.

DESCRIPTION OF THE DRAWINGS

The invention will be described with particular reference to the drawings in which.

DETAILED DESCRIPTION

Figure 1:
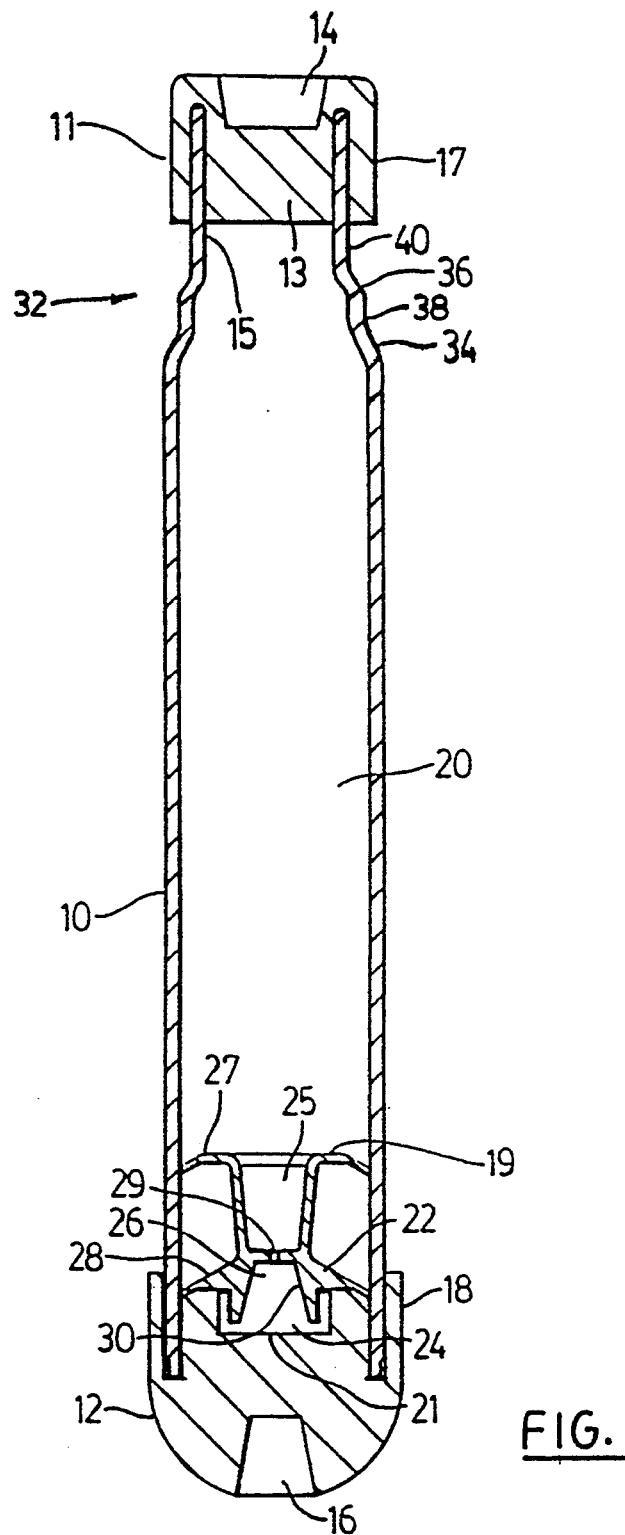
FIG. 1 is a schematic representation of a cross-sectional area of one embodiment of the tube.

Referring to FIG. 1, tube 10 (which may also be known as or referred to as a vial) is shown as having a first end cap 11 and a second end cap 12. As shown, the end caps are of different construction. Apart from end section 32 near first end cap 11, tube 10 has a substantially constant diameter, and constant cross-section, throughout the major portion of its length. End section 32 represents a minor portion of the length of tube 10.

First end cap 11 is comprised of a plug 13 having recess 14. Plug 13 fits inside tube 10 and forms a fluid and vacuum tight seal with the inner surface 15 of tube 10, so as to form a fluid tight closure with tube 10. First end cap 11 also has rim 17 that fits tightly onto the outside of tube 10. In addition, the exposed end of first end cap 11 is shown as having a flat end, which could be used to stand the tube in a vertical position. In contrast, second end cap 12 is shown as having a rounded exposed end. The shape of the end of end caps 11 and 12 is not critical.

Second end cap 12 is shown as having recess 16, which is axially located in the end cap. In addition, second end cap 12 has rim 18 which fits over the end of tube 10 to form a fluid and gas tight seal therewith. It will be appreciated that there are variations in the type of end cap that may be used. In embodiments, the end cap is accompanied by a stopper or plug, with the stopper or plug providing the fluid and gas tight seal and the end cap being for protection and/or to retain the stopper or plug in place.

The separation device in tube 10 is generally indicated by 19. Separation device 19 divides the space within tube 10 into first chamber 20 and second chamber 21; it is to be understood that in embodiments of the invention, end cap 12 contacts and seats with separation device 19 such that second chamber 21 is in effect an incipient chamber which forms into chamber 21 on movement of separation device 19, within tube 10, away from end plug 12. Separation device 19 is comprised of separation shell 22 and plug 24. Separation shell 22 has a first shell recess 25 disposed towards first chamber 20 and second shell recess 26 disposed towards second chamber 21; first shell recess 25 may contain a filter (not shown). Separation shell 19 also has first flange 27 and second flange 28, which in the embodiment shown are non-planar curved surfaces that extend to and are in sliding engagement with inner wall 15 of tube 10, and form an effective fluid tight seal therewith; flanges of other shapes may be used. While two flanges are shown, and are preferred, it is believed that at least one flange is required. Plug 24 is located in second shell recess 26. The inner surface 30 of recess 26 has a convoluted path formed in the surface thereof which, in conjunction with the surface of plug 24, forms a channel (not shown) that is in fluid flow communication between opposite ends of plug 24. Separation shell 19 is shown as having an axial orifice 29 for flow of fluid.

End section 32 of tube 10 is of smaller diameter than tube 10. In the embodiment shown, the reduction in diameter of tube 10 is in two stages, forming tapered sections 34 and 36 and straight sections 38 and 40; straight section 38 is located between tapered sections 34 and 36, and straight section 40 forms the end of the tube on which is located end cap 11. The walls of straight sections 38 and 40 are preferably parallel to the longitudinal axis of tube 10, and are used for optical monitoring of the separation of the phases, as discussed below. This is contrary to the tubes described in the aforementioned applications of Adams and Luoma and of Luoma in which the space between first flange 27 and second flange 28 of separation device 19 is used for optical monitoring of the separation process. It is understood herein that optical monitoring includes both visible and non-visible sections of the electromagnetic spectrum i.e. it includes use of the visible spectrum, as well as infrared and ultra violet wavelengths.

Plug 24 would normally be made from a rigid plastic with requirements with respect to a method of operation described herein, during movement of the separation device 19 within tube 10. End caps will normally be relatively rigid plastic, depending on whether penetration by needles is required. Plugs or stoppers may be rigid or elastomeric, including self-sealing elastomeric, again depending on the particular intended mode of operation. The self-sealing materials referred to herein, especially with respect to the end caps, are known in the art of blood collection tubes.

Figure 2:
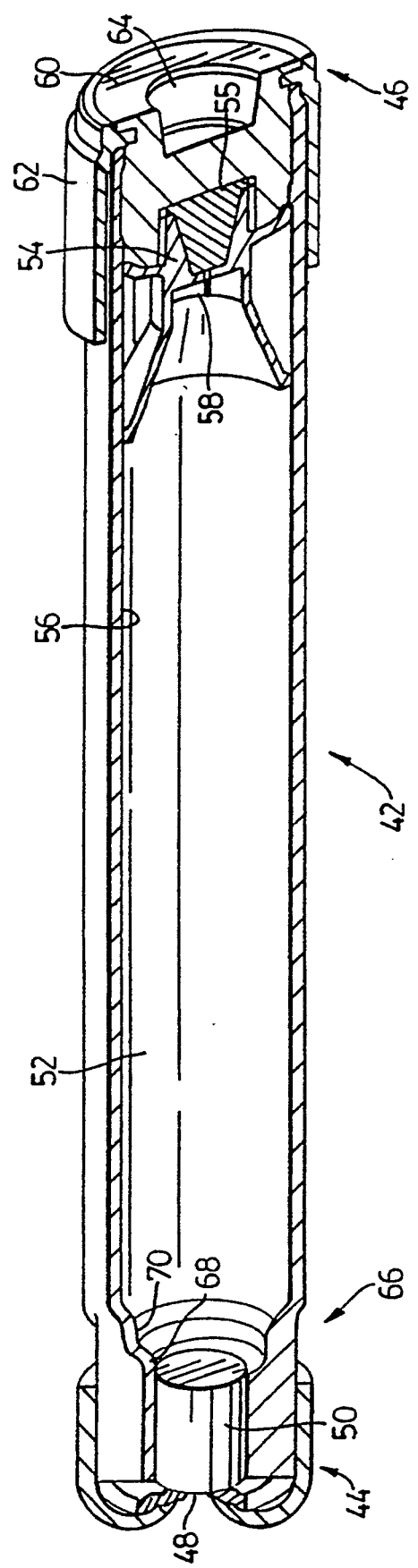
FIG. 2 is a schematic representation of a cross-sectional area of another embodiment of the tube.

FIG. 2 shows another embodiment of the tube. Tube 42 has a first end 44 and a second end 46. First end 44 is shown as having a recessed orifice 48 containing plug 50. Recessed orifice 48 is shown as being moulded as part of first end 44, and is located on the longitudinal axis of tube 42. First chamber 52 is located between plug 50 and separation device 54. Separation device 54 is in sliding engagement with wall 56 of tube 42, and has axial orifice 58 for flow of fluid from first chamber 52 to a second chamber. In the embodiment shown in FIG. 2, the second chamber is an incipient chamber that forms on movement of separation device 54 along tube 42 towards first end 44, but the second chamber could exist at all times. As shown, the incipient second chamber, 55, is located between, and at the mating surface of, separation device 54 and end cap 60 in second end 46. End cap 60 has rim 62 that fits over the outside of tube 42 and holds end cap 60 in position, as well as end cap recess 64 which is used during movement of the separation device and removal of fluid from the tube. It will be noted that end cap 60 has a flat end, whereas second end cap 12 of FIG. 1 has a rounded end; these shapes represent two embodiments of the end caps that may be used.

FIG. 1 and FIG. 2 show two different types of end caps adjacent to the first chamber viz. first end cap 11 and recessed orifice 48 with plug 50. It is to be understood that other end caps may be used, including grommets, the principal requirement being that the resultant tube meet all physical, functional and regulatory requirements for the intended use.

A separation device is described in greater detail in the aforementioned copending patent application of G. A. Adams and R. P. Luoma.

First end 44 of tube 42 is shown as having a tapered section generally indicated by 66, which as shown is similar in design to that shown in FIG. 1. Straight sections 68 and 70 have walls that are shown as being parallel to the longitudinal axis of tube 42, which is preferred for optical monitoring, and need to be optically transparent to permit monitoring.

In operation, a sample of liquid having phases of differing densities e.g. blood, is placed in the tube; the operation of the method of the invention will generally be described herein with reference to separation of blood into a cell fraction and a non-cellular fraction. The blood is inserted into first chamber 20. In the embodiment of FIG. 1, this may be done by removing first end cap 11 and inserting the blood. However, for safety reasons, blood is normally drawn directly into first chamber 20, as a consequence of having a vacuum inside first chamber 20, using a needle.

The separation device is particularly intended for use in an axial centrifuge e.g. an axial centrifuge of the type described in the aforementioned U.S. Pat. No. 4,828,716. The separation device is rotated about its longitudinal axis to effect phase separation. When separation is complete, the high density, concentrated, clotted cells are located near the tube wall and the lower density non-cellular fraction e.g. serum (and any air or other gases) are located closer to the longitudinal axis. A probe then penetrates second end cap 12 and contacts and is resisted by plug 24. Further force by the probe causes the separation device to become detached from second end cap 12 and to move along tube 11, thereby decreasing the volume of first chamber 20. This decrease in volume results in the material located on the longitudinal axis flowing through access channel 29, along the convoluted path located at the interface between plug 24 and separation shell 19 and into second chamber 21. Air or other gaseous matter is the first to flow into second chamber 21, followed by the non-cellular fraction.

An optical sensor is located exterior to the tube and in a fixed location opposite straight section 40 of tube 10. During axial spinning, the blood cell separate and locate on the walls of the tube. As the separation device 19 moves down the tube, the decreasing volume available to the blood cells results in the layer of blood cells on the wall becoming increasingly thick. The thickness will increase until blood cells start to locate on straight wall 40. At this time, the optical sensor detects the presence of the cells and causes the movement of the probe to stop. Thus, the blood cells do not enter second chamber 21. The probe is withdrawn while the tube is still being rotated about its axis, with the result that the probe does not become contaminated by the sample in the tube. It is believed that the probe is capable of being used on a subsequent sample without cross-contamination of samples.

A similar mode of operation is used for the embodiment of FIG. 2.

Figure 3A:
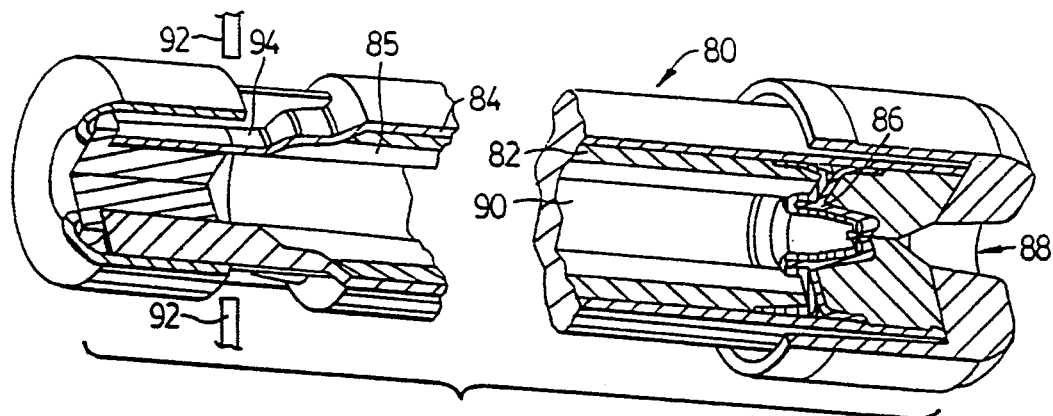
FIGS. 3A, 3B and 3C are schematic representations showing an embodiment of the tube during separation of a sample of blood.

The use of the tubes in the separation of blood is illustrated in FIG. 3. In FIG. 3A, tube 80 is shown as being axially spun, with blood cells 82 being located along wall 84 and serum 85 being more axially located than blood cells 82, within first chamber 90 of tube 80. Separation device 86 is shown as still being located at second end 88 of tube 80. An optical sensor 92 is shown as being in a fixed location opposite straight wall 94 of tube 80.

Figure 3B:
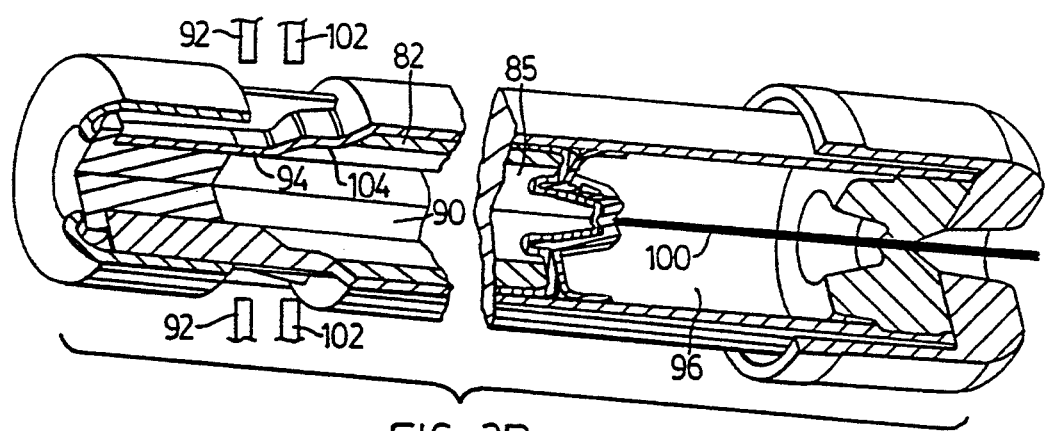

In FIG. 3B, separation device 86 has been moved partially down tube 80 by probe 100. The thickness of the layer of blood cells 82 has increased. Serum is still located in only first chamber 90. Second chamber 96 contains air that was in the sample of blood, as air is the fluid that is axially located in first chamber 90 during initial axial spinning and thus is the first fluid to pass through the separation device 86 as it moves along tube 80. Optical sensor 92 is still located opposite straight wall 94, as it is throughout the separation process.

FIG. 3B also shows an embodiment having a second optical sensor 102 that is opposite second straight wall 104 of tube 80; second straight wall 102 is adjacent straight wall 94, being separated therefrom by a tapered section, at a section of tube 80 that has a greater diameter than at straight wall 94 i.e. second straight wall 102 corresponds to straight section 38 of FIG. 1 and straight wall 94 corresponds to straight section 40 therein. The embodiment with second optical sensor 102 is only illustrated in FIG. 3B, for simplicity, but it represents a second means to monitor the separation of phases within the tube. Thus, multiple monitoring of separation of phases may be accomplished using tubes with suitable multiple straight wall sections and accompanying optical sensors, and the multiple phases could be removed or sampled in sequence from second chamber 96.

Figure 3C:
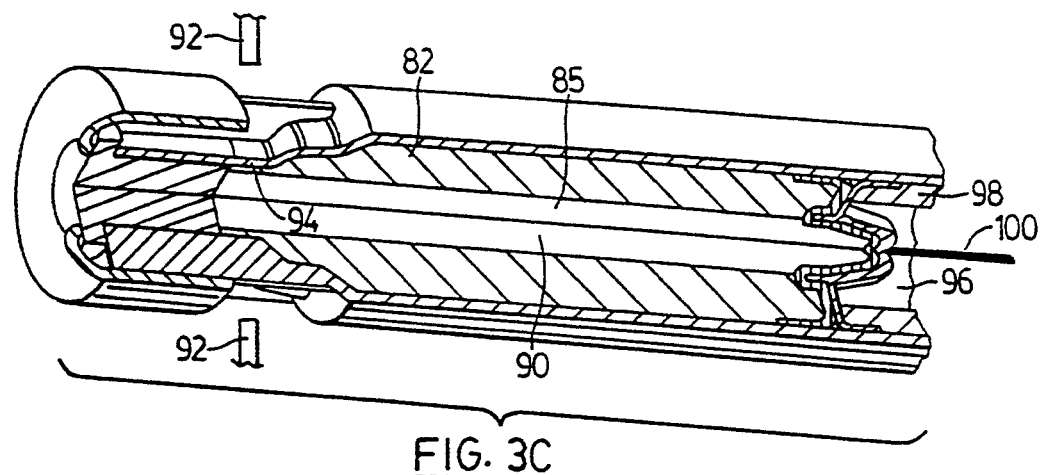

In FIG. 3C, separation device 86 has moved further down tube 80. The thickness of the layer of blood cells 82 has now increased to the point where blood cells are located at straight wall 94. Optical sensor 92 detects the onset of the presence of blood cells on straight wall 94 and causes probe 100 to stop moving down tube 80, and to actually withdraw from tube 80. The movement of probe 100 may be stopped instantaneously, or effectively so, or movement of probe 100 may have a predetermined delay prior to cessation of movement to effect more separation of serum into second chamber 96, the amount of predetermined delay being a function of the design of tube 80 and separation device 86. Serum is shown as located in both first chamber 90 and second chamber 96, the latter being designated 98.

The tube is made of an optically transparent material e.g. glass or Selar ® polyamide, which is manufactured by E. I. du Pont de Nemours and Company of Wilmington, Del. U.S.A. Other optically transparent materials may be used, prime requirements being acceptable transparency and sufficient strength to withstand the forces applied in a centrifugation process. In addition, the tube must be capable of retaining a vacuum, a capability of retention of vacuum for a period of about 2 years being preferred. Tubes or vials of acceptable properties are known and used in the collection and processing of blood. The separator shell may be moulded from thermoplastic or other polymers, a prime requirement being that the polymer not have adverse effects on the properties and characteristics of the blood and the components thereof. In addition, the separation device needs to provide an adequate fluid seal against the side of the tube in which it is located, and be capable of being fabricated into the shape of the separation device. An example of a suitable material is polypropylene.

The material used in the fabrication of the plugs will depend in particular on the mode of operation of the process. In the method particularly described herein, a probe exerts pressure on plug 24 in order to move the separation device along the tube. Such pressure must not cause blockage of passages used for flow of fluid from the first chamber to the second chamber, and the material selected for fabrication of the plug must take this requirement into account. In addition, the material of the plug must not adversely affect the fluid in the tube or results of any tests or analyses conducted on that fluid or its components. Ethylene/vinyl acetate polymer, polypropylene and polyamide compositions have been found to be acceptable, including Elvax ® 250, 260, 450 and 550 and Selar ® polymer compositions available from E. I. du Pont de Nemours and Company, but other compositions will become apparent to persons skilled in the art; it is believed that polycarbonate and stainless steel could be used.

The end caps need to be made from a self-sealing material, especially a self-sealing elastomeric material. Examples of such materials are known in the art.

It is preferable that fluid not flow back from second chamber 21 into first chamber 20 after the centrifuging, especially axial centrifuging, of the tube has ceased, but it is more important that fluid not continue to flow, albeit intermittently, from first chamber 20 into second chamber 21. In particular, it is important that in-use handling, including shaking and tipping of the tube, does not result in flow of fluid in either direction, especially not flow of the cell fraction from chamber 20 into chamber 21. Fluid flow paths having such characteristics are known, for example the convoluted path described in the aforementioned copending application of Adams and Luoma.

The double-ended separation tube of the present invention has a minimal number of independent parts, resulting in few critical mating surfaces and connections, for improved consistency and reliability from tube to tube. A particularly important aspect of the invention is that the drawing of blood or other fluid into the tube is physically separated from the removal of samples from the tube. Thus, the blood is drawn into one end of the tube and the samples are withdrawn from the other end of the tube. This eliminates possible contamination of the sample by blood as a result of droplets of blood remaining in or on plugs or end caps, or the like, through which needles are passed during drawing of blood; in the present invention this occurs at the opposite ends of the tube, thereby eliminating that source of contamination. The tube is particularly intended to be used in an axial centrifuge having an optical sensor in a fixed position, as defined in the method described herein, which is an important simplification of the method and associated apparatus. A practical tube accomplishing these advantages is described herein, especially with respect to axial centrifugation separation processes.

The tubes of the present invention do not require gaps in labels to permit optical monitoring as is required by other known designs. In addition, the used of fixed sensing devices reduces the complexity of the apparatus in which the tube is used. The fixed sensing may be of a through-beam type or a reflective type, and simple optical paths may be used, again increasing reliability in use.

A filter may be used in first shell recess 25 to filter fluid passing through that recess to the axial orifice. For example, platelets could be filtered from the blood fraction passing through the axial orifice.

It is understood that the tubes may contain anticoagulants or clot activators, as is known in the art.

Although the tube and separation device have been described herein with reference to axial centrifugation, at least some tubes and separation devices described herein are also capable of being used in conventional centrifuges. It is to be understood, however, that the separation device may not function in the manner described herein even though the tube containing the separation device is usable.

I claim:

1. A tube adapted for the partitioning and separation of a pre-selected phase of a sample of liquid having a plurality of phases of differing densities and optical characteristics, said tube being linear and having sealable openings at first and second opposed ends thereof, the first end of the tube having a section of smaller diameter than the second end said section being configured to facilitate monitoring of the optical characteristics, said smaller diameter section extending away from the sealable opening at the first end for a minor fraction of the length of the tube and being optically transparent, a separation device located within the tube that separates the tube into at least two chambers at opposed ends of the tube, said separation device being slidably engaging the interior surface of the tube in an essentially fluid-tight manner, the separation device having an orifice therethrough for fluid flow communication between the chambers, said orifice having a flow-restriction channel.

2. The tube of claim 1 in which said minor fraction of the length of the tube has walls that in part are parallel to the longitudinal axis of the tube.

3. The tube of claim 2 in which the tube at locations other than the first end is of constant diameter and cross-section.

4. The tube of claim 3 in which the second chamber is an incipient chamber that forms as the separation device is moved along the tube and away from the first end.

5. The tube of claim 3 in which the first end is transparent to the visible spectrum.

6. The tube of claim 3 in which at least a portion of the tube is transparent to at least one of the infrared and ultraviolet spectrums.

7. The tube of claim 3 in which the tube is adapted for the separation of a phase from blood.

8. A method of partitioning a pre-selected phase of a sample of liquid having a plurality of phases of differing densities and optical characteristics, comprising the steps of:

(a) passing said sample of liquid through a first end of a linear tube and into a first chamber of said tube, said first chamber being located at the first end of said tube and being separated from a second chamber located at a second opposed end of said tube by a separation device, said first end and said second end having sealable openings, said second chamber being free of the liquid, said separation device slidably engaging the interior surface of the tube in an essentially fluid-tight manner and having a flow-restriction orifice therein to permit fluid flow communication between the first and second chambers under the influence of force, said first end of the tube having a section of smaller diameter than the second end, said smaller diameter section extending away from the sealable opening at the first end for a minor fraction of the length of the tube;

(b) ordering the phases of the sample within the tube using axial centrifugation;

(c) while the phases are ordered, reducing the volume of the first chamber by movement of the separation device within the tube, such that one phase of the liquid in the first chamber flows through the flow-restriction orifice as the volume of the first chamber is reduced and into the second chamber, said phase in the second chamber being removable therefrom through the second end of the tube; and (d) monitoring at least one phase so ordered by optical means fixedly located opposite the section of the tube of smaller diameter and controlling the reduction in volume in accordance with the results of the monitoring of said phase.

9. The method of claim 8 in which said minor fraction of the length of the tube into which the sample is passed has walls that in part are parallel to the longitudinal axis of the tube.

10. The method of claim 9 in which the tube into which the sample is passed is, at locations other than the first end, of constant diameter and cross-section.

11. The method of claim 10 in which the flow-restriction orifice permits flow of liquid from the first chamber to the second chamber during step (c) but restricts flow of liquid at other times.

12. The method of claim 10 in which the second chamber is an incipient chamber that forms as the separation device is moved along the tube.

13. The method of claim 10 in which the liquid is blood, or a fraction thereof, and serum or plasma is separated.

14. The method of claim 10 in which the optical means uses the visible spectrum.

15. The method of claim 10 in which the optical means uses at least one of the infrared and ultraviolet spectrums.

16. The method of claim 10 in which a phase is separated from blood.

17. The method of claim 10 in which more than one phase is monitored.

* * * * *